United States Patent [19]

Matsuura et al.

[11] Patent Number: 5,177,015

[45] Date of Patent: Jan. 5, 1993

[54] ONCO-DEVELOPMENTALLY REGULATED α-N-ACETYLGALACTOSAMINYLTRANSFERASE

[75] Inventors: Hidemitsu Matsuura; Sen-itiroh Hakomori, both of Seattle, Wash.

[73] Assignee: Fred Hutchinson Cancer Research Centre, Seattle, Wash.

[21] Appl. No.: 825,308

[22] Filed: Jan. 22, 1992

Related U.S. Application Data

[63] Continuation of Ser. No. 231,576, Aug. 12, 1988, abandoned.

[51] Int. Cl.$^5$ .......................... C12N 9/10; C12Q 1/48
[52] U.S. Cl. ........................................ 435/193; 435/15
[58] Field of Search .................................. 435/193, 15

[56] References Cited

PUBLICATIONS

Hearn et al, *Biosynthesis of Blood Gropu Active Glycoproteins* . . . , BBRC, 41, No. 5, 1970.
Kijimoto et al, *Biosynthesis of Forssman Hapten* . . . , BBRC, 56, No. 1, 1974.
Ishihashi et al, *Solubilization and Partial Characterization* . . . , Biochim et Biophsy. Acta, 484, pp. 24–34, 1977.
Lowe et al, *Purification and Properties of an* . . . , Wash. Univ. St. Louis, Abstract Conference of American Society of Cell Biology, 1986.
Das et al, *Biosynthesis in vitro of a Globoside* . . . , 149, pp. 119–135, 1986, Carbohydrate Research.
Taniguchi et al, *Expression of Forssman Antigen*; JNCI, 67, No. 3, pp. 577–583, 1981.
Taniguchi et al, *Globoside and Forssman Synthesis* . . . , JNCI, 74, No. 3, pp. 563–568, 1985.
Ishibashi et al, *Effects of Uridine Nucleotides* . . . , Biochim. et Biophys. Acta, 429, pp. 759–767, 1976.
Taniguchi et al, *UDP-N-Acetylgalactosamin:globoside* . . . , Journ. of Biol. Chem. 257, No. 18, pp. 10631–10637, 1982.

(List continued on next page.)

Primary Examiner—David M. Naff
Assistant Examiner—Mike Meller
Attorney, Agent, or Firm—Christensen, O'Connor, Johnson & Kindness

[57] ABSTRACT

An onco-developmentally regulated α-N-acetylgalactosaminyltransferase is isolated as a component of a particulate membrane fraction separated from cell and tissue homogenates which has the following characeristics:

(a) Activity in Various Cells and Tissues—present in human fetal lung fibroblasts, hepatoma tissues and placenta, but absent from normal adult liver, lung, kidney and spleen tissues;

(b) Substrate Specificity—acts on polypeptides comprising a sequence of val-thr-his-pro-gly-tyr by catalyzing α-N-acetylgalactosaminylation at the thr residue of the sequence;

(c) Requirements for Metal Ion—requires metal ion for activity in 25 mM tris buffer, pH 7.6;

(d) Optimal pH—optimal pH is about 7.6 asssayed in hepatoma cell homogenate in tris buffer and at a pH of about 6 to about 7 assayed in hepatoma cell homogenate enzyme activity is higher in 2(N-morpholino)ethanelsulfonic acid than in cacodylate buffer; and (e) Km—apparent Km for UDP - GalNAc is about 48 μm. The alpha-N-acetylgalactosaminyltransferase is used in a method of detecting tumor cells.

Also, a diagnostic test kit for detecting tumor cells in a sample suspected of containing tumnor cells is disclosed containing as separate components:

(a) labeled α-N-acetylgalactosamine; and
(b) polypeptide substrate comprising a sequence of val-thr-his-pro-gly-tyr.

1 Claim, 2 Drawing Sheets

PUBLICATIONS

Kijimoto-Ochai et al, *Mechanism for the Biosynthesis . . .*, J. of Biol. Chem., 255, No. 19, pp. 9037-9040, 1980.

Gooi et al., *Differing Reactions of Monoclonal Anti-A . . .*, J. of Biol. Chem., 260, No. 24, pp. 13218-13224, 1985.

Takasaki et al, *Chemical Characterization and Distribution . . .*, J. of Biol. CHem. 251, No. 12, pp. 3610-3615, 1976.

Yoda et al, *Isolation, Characterization and Biosynthesis . . .*, J. Biochem., 88, pp. 1887-1890, 1980.

Cartron et al, *Study of the α-N-Acetylgastosaminyltrans . . .*, J. of Immunogenetics, 5, pp. 107-116, 1978.

Yokosawa et al, *Studies on Aminoglycolipid Contents . . .*, Biochim. et Biophys. Acta, 528, pp. 138-147, 1978.

Bhavanadan et al, *Characteristics of a Main-Type . . .*, BBRC, 70, No. 1, 1976.

Chemical Abstracts, vol. 97, No. 7, Aug. 16, 1982, p. 438, No. 543417A.

Chemical Abstracts, vol. 107, No. 19, Nov. 9, 1987, p. 504, No. 173502W.

Journal of Biological Chemistry, vol. 264, No. 18, Jun. 25, 1989, pp. 10472-10476.

Journal of Biological Chemistry, vol. 249, No. 11, Jun. 10, 1974, pp. 3442-3447.

Matsuura H., and Hakomori S. (1985) *Proc. Natl. Acad. Sci.* vol. 82, pp. 6517-6521.

Matsuura, H., et al (1988) *J. Biol. Chem.* 263, 3314-3322.

ONCO-DEVELOPMENTALLY REGULATED α-N-ACETYLGALACTOSAMINYLTRANSFERASE

FIELD OF THE INVENTION

The present invention relates to a new onco-developmentally regulated α-N-acetylgalactosaminyltransferase and to a method for detecting tumor cells by assaying for the enzyme activity in tissue homogenate.

BACKGROUND OF THE INVENTION

Oncofetal antigens are structures expressed during specific stages of embryogenesis and fetal development. Their expression declines during oncogenesis and is suppressed in most established adult tissues, with a few exceptions. Some polypeptide oncofetal antigens. such as α-fetoprotein, are primary gene products highly expressed at specific stages of embryogenesis, and their synthesis is repressed in adult tissue. In such cases, in which the state of de-differentiation is associated with cancer, dormant genomes may become de-repressed, and fetal antigens may reappear as an index of neoplastic transformation (Sulitzeanu, D. (1985) *Advances in Cancer Research*, Klein G. and Weinhouse S. (ed.) Academic Press. New York. 44, 1-31).

By application of the monoclonal antibody approach, a number of oncodevelopmentally regulated antigens have been identified as carbohydrates, particularly as extended globo-series structures (Hakomori S. and Kannagi R. (1983) *J. Natl. Cancer Inst.* 71, 231-251 and Kannagi R., et al. (1983) *J. Biol. Chem.* 258, 8934-8942), fucosylated and fucosylated-sialylated lactoseries structures (Hakomori S. and Kannagi R. (1983) *J. Natl. Cancer Inst.* 71, 231-251, Fukushi Y., Hakomori S., and Shepard T. (1984) *J. Exp. Med.* 159, 506-520 and Fukushi Y., et al. (1985) *Cancer Res.* 45, 3711-3717). Since these carbohydrate antigens are secondary gene products and their expression is controlled by concerted action and organization of glycosyltransferases, the genetic basis for their expression remains unknown.

One group of oncodevelopmentally regulated antigens is comprised of fibronectins.

Fibronectins (FNs) are disulfide-linked dimers of 250-kDa subunits, and play an important role in various contact processes, such as cell attachment and spreading, cell migration, embryonic development, wound healing, hemostasis, opsonization, and oncogenic transformation (Yamada, K. M. (1983) *Ann. Rev. Biochem.* 52 761-799). Two major isotypes of FN have been known; one (plasma FN) is found in plasma and the other (cellular FN) is present in the pericellular matrix and is secreted into the culture medium of fibroblasts. The exact sequence and domain structure of both plasma FN and cellular FN have been fully described, and the genetic mechanism yielding such FN isotypes has been investigated (Hynes, R. O. (1985) *Annu. Rev. Cell Biol.* 1, 69-90). Both FNs are two different products of a single gene (Kornblihtt, A. R., et al. (1983) *Proc. Natl. Acad. Sci. USA* 80, 2318-3222) and each subunit has three different types of internal repeats (homology types I, II, and III) (Petersen, T. E., et al. (1983) *Proc. Natl. Acad. Sci. USA* 80, 137-141). The primary structural differences between the subunits are the result of a complex pattern of alternative splicing of the precursor mRNA. To date, three regions, designated as IIICS, EDI, and EDII, of alternative splicing have been identified (Gutman, A. and Kornblihtt. A. R. (1987) *Proc. Natl. Acad. Sci. USA* 84, 7179-7182). The IIICS (type III connecting segment) region is located between the penultimate and the last type III repeats, i.e. between, the Hep-2 and Fib-2 domain.

Additionally, monoclonal FDC-6 was established, which reacts specifically with cellular FN but not with plasma FN. FNs extracted from normal adult tissues do not react with this antibody. In contrast, FNs isolated from various fetal tissues, amniotic fluid, and placenta as well as from various types of human carcinomas and sarcomas and their cell lines are found to react with FDC-6 (Matsuura, H. and Hakomori, S. (1985) *Proc. Natl. Acad. Sci. USA* 82 6517-6521). Thus, a new concept developed that FNs are clearly defined with two classes which can be distinguished by monoclonal antibody FDC-6 and which are related in much the same way as α-fetoprotein (AFP) to albumin and carcinoembryonic antigen (CEA) to nonspecific cross-reacting antigen (NCA): (i) oncofetal FN (onfFN) derived from cancer and fetal cells and tissues, and previously known as cellular FN, and (ii) normal FN (norFN) derived from normal adult tissues and plasma, and previously known as plasma FN (Matsuura, H. and Hakomori, S. (1985) *Proc. Natl. Acad. Sci. USA* 82 6517-6521).

The minimum essential structure required for the FDC-6 reactivity was found to be a hexapeptide sequence, val-thr-his-pro-gly-tyr, having NeuAcα2->3-Galβ1->3-GalNAc or its core (Galβ1->3GalNAc or GalNAc) linked at a defined threonine residue of the IIICS region, which is a naturally-occurring polypeptide portion. Further, α-N-acetylgalactosaminylation using hepatoma cells converted the synthetic peptide including defined hexapeptide, which has no reactivity with FDC-6, into a reactive one.

Evidence for oncodevelopmentally-regulated α-N-acetylgalactosaminyltransferase has not been presented, Furthermore, the difference between α-N-acetylgalactosaminyltransferase in cancer, fetal, and normal adult tissues is unknown. Accordingly, it would be advantageous to (1) isolate the primary gene product, oncodevelopmentally-regulated α-N-acetylgalactosaminyltransferase, and to establish that the enzyme is present and responsible for transferring GalNAc to a defined polypeptide chain in fetal, placental, and tumor tissue, but not in normal adult tissue; and (2) provide a biochemical assay for detecting the presence of this enzyme as an indication of transforming tissue at an early stage in oncogenesis.

SUMMARY OF THE INVENTION

Accordingly, one object of the present invention is to provide a new tumor-associated α-N-acetylgalactosaminyltransferase the activity of which can readily be assayed in tissue homogenates.

A second object of the present invention is to provide a method for using the enzyme as a tumor maker.

These and other objects have been achieved by providing onco-developmentally regulated α-N-acetylgalactosaminyltransferase isolated as a component of a particulate membrane fraction separated from cell and tissue homogenates and having the following characteristics:

(a) Activity in Various Cells and Tissues—present in human fetal lung fibroblasts, hepatoma tissues and placenta, but absent from normal adult liver, lung, kidney and spleen tissues;

(b) Substrate Specificity—acts on polypeptides comprising a sequence of val-thr-his-pro-gly-tyr by catalyzing α-N-acetylgalactosaminylation at the thr residue of the sequence;

(c) Requirements for Metal Ion—requires metal ion for activity in 25 mM tris buffer, pH 7.6;

(d) Optimal pH—optimal pH is about 7.6 assayed in hepatoma cell homogenate in tris buffer and at a pH of about 6 to about 7 assayed in hepatoma cell homogenate enzyme activity is higher in 2(N-morpholino)ethanesulfonic acid than in cacodylate buffer; and (e) Km—apparent Km for UDP-GalNAc is about 48 μM.

The present invention also provides two methods of isolating the onco-developmentally regulated α-N-acetylgalactosaminyltransferase.

One method of isolation comprises the steps of:

(1) contacting oncofetal tissue with an immobilized polypeptide comprising a sequence of val-thr-his-pro-gly-tyr to thereby form an affinity complex between the α-N-acetylgalactosaminyltransferase and the polypeptide;

(2) washing the complex; and (3) eluting the α-N-acetylgalactosaminyltransferase from the immobilized polypeptide.

The other method of isolation comprises the steps of:

(1) labeling a polypeptide comprising a sequence of val-thr-his-pro-gly-tyr with a detectable marker;

(2) reacting the polypeptide with a bifunctional photoreactive cross-linking agent;

(3) contacting the reacted polypeptide with an oncofetal tissue homogenate;

(4) exposing the tissue homogenate of step (3) to ultraviolet radiation, thereby cross-linking the labeled polypeptide to α-N-acetylgalactosaminyltransferase present in said homogenate; and (5) purifying the labeled polypeptide cross-linked to the α-N-acetylgalactosaminyltransferase.

In a further aspect the present invention provides a method of detecting tumor cells.

The method of detecting tumor cells comprises the steps of:

(1) homogenizing tissue suspected of having tumor cells;

(2) incubating the homogenate with labeled α-N-acetylgalactosamine (α-GalNAc) and a polypeptide substrate comprising a sequence of val-thr-his-pro-gly-tyr under conditions sufficient to catalyze α-N-acetylgalactosaminylation of the thr residue to thereby form labeled polypeptide substrate comprising val-thr(α-GalNAc)-his-pro-gly-tyr; and (3) determining the presence of said labeled polypeptide substrate.

In an even further aspect, the present invention provides a diagnostic test kit for detecting tumor cells comprising as separate components:

(a) labeled α-N-acetylgalactosamine, and (b) polypeptide substrate comprising a sequence of val-thr-his-pro-gly-tyr.

In the methods of isolating onco-developmentally regulated α-N-acetylgalactosaminyltransferase, in the method of detecting tumor cells and in the diagnostic test kit, it is particularly advantageous for the polypeptide substrate to be thr-pro-phe-val-thr-his-pro-gly-tyr-asp-thr-gly-asn-gly-ile. Also the monoclonal antibody FDC-6 is preferred as a means for separating the reacted product from the reaction mixture in order to detect labeled product. A preferred labeled α-N-acetylgalactosamine is UDP[$^3$H]-GalNAc.

A. Effect of pH. Hepatoma cell homogenate was prepared as described in Example 2 and reacted with the synthetic peptide thr-pro-phe-val-thr-his-pro-gly-tyr-asp-thr-gly-asn-gly-ile (TPI) as described in Example 2, using different buffer solutions; i.e., 25 mM MES (2(N-morpholino)ethanesulfonic acid, Sigma Chemical Co.), pH range 5.4–7.0; 25 mM cacodylate. pH range 5–7; 25 mM HEPES (N-2-hydroxyethylpiperazine-N'-2-ethanesulfonic acid, Sigma), pH range 7–8; or Tris, pH range 7–9, in the presence of 10 mM MgCl$_2$ and 1 mM CaCl$_2$.

B. Effect of UDP-GalNAc concentration. A Hanes-Woolf plot of saturation data was obtained by varying UDP-GalNAc concentration from 0.6 μM to 200 μM. The reaction was conducted as described in Example 2 in the presence of 100 mg protein and 200 nmol TPI. The specific activity of UDP[$^3$H]-GalNAc utilized was $4 \times 10^6$ cpm/nmol.

C. Variation of incubation time. The standard reaction mixture described in Example 1 using TPI was incubated for 10 min to 24 hr. open circles, with TPI; closed circles, without TPI (control).

Figure 2:
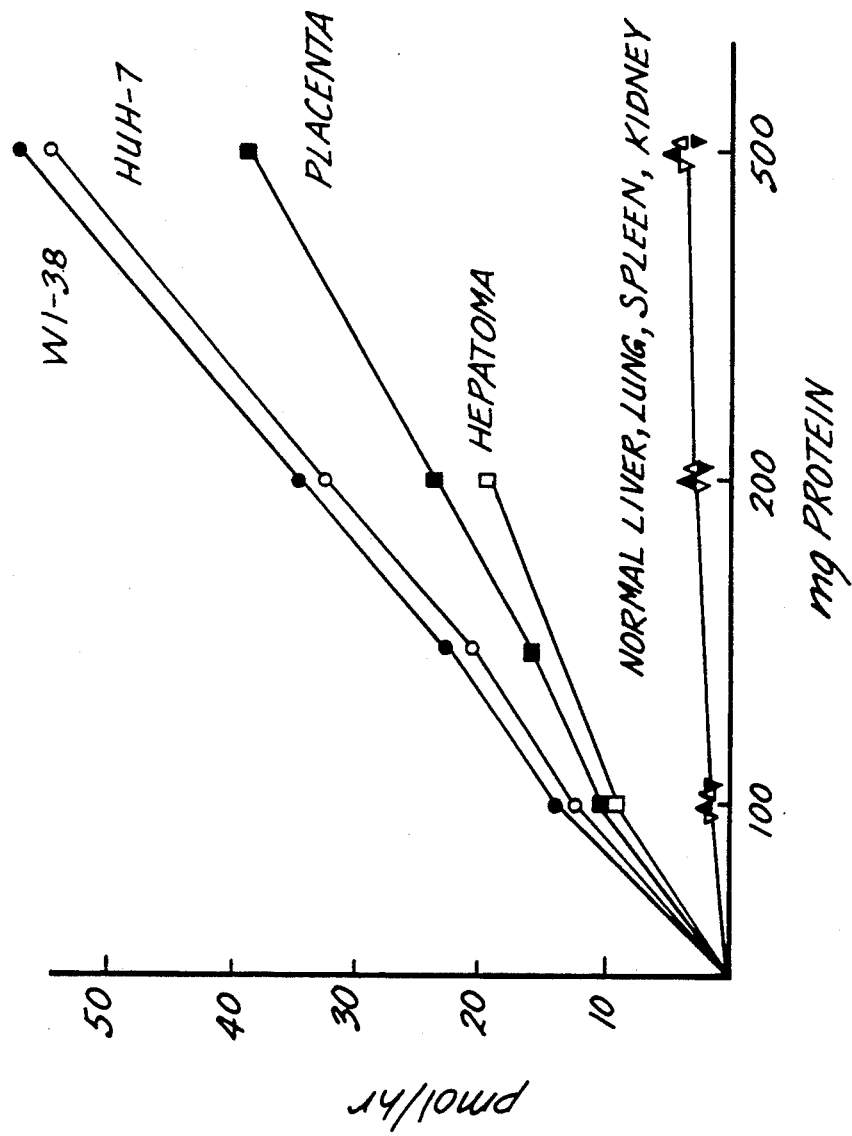

FIG. 2 is a graph showing onco-developmentally regulated α-N-acetylgalactosaminyltransferase activity in various cells and tissues. Human placenta, hepatoma, normal adult liver, lung, spleen, and kidney were homogenized and used as an enzyme source. Multiple concentrations of each tissue protein were incubated with TPI under the conditions described in Example 4. The activity of HUH-7 and human fetal lung fibroblast (WI-38) are also shown.

DETAILED DESCRIPTION OF THE INVENTION

The present invention derives from the discovery by the present inventors of a new class of onco-developmentally regulated epitope, in which conformation of a naturally-occurring polypeptide sequence was greatly altered by a single glycosylation to form an oncofetal structure. Glycosylation induces the oncofetal polypeptide epitope, yet glycosylation per se does not carry the epitope. This was demonstrated with an oncofetal fibronectin defined by the monoclonal antibody FDC-6.

An extensive study on chemical identification of FDC-6 reactive epitope structure clearly demonstrated that the minimum essential structure for FDC-6 reactivity is the hexapeptide sequence val-thr-his-pro-gly-tyr (VTHPGY) having NeuAc$_{\alpha 2-3}$Gal$_{\beta 1-3}$GalNAc or its core (Gal$_{\beta 1-3}$GalNAc or GalNAc) linked at a defined threonine residue of the IIICS region which is a normally occuring polypeptide region. Further neither the carbohydrate residues nor the peptide per se is able to form epitope directed to FDC-6 (Matsuura, H., et al. (1988) J. Biol. Chem. 263, 3314–3322). The crucial oncofetal change induced in onfFN is α-GalNAc transfer to the threonine residue of the VTHPGY sequence, which is present at the IIICS region in both onfFN and norFN.

Since the epitope expression of onfFN is regulated by α-N-acetylgalactosaminyltransferase, onfFN is a secondarily expressed oncofetal antigen, as are most of the oncofetal carbohydrate antigens (Hakomori, S. (1984) Ann. Rev. Immunol. 2, 103–126). This is in contrast to oncofetal protein antigens such as α-fetoprotein and carcinoembryonic antigen, which are primary gene products.

α-N-acetylgalactosaminyltransferase has been well established in biosynthesis of a common core structure of O-linked carbohydrate chains in mucin-type glycoproteins and other membrane and serum glycoproteins (Schacter, H. and Roseman, S. In: "The biochemistry of glycoproteins and proteoglycans" (Lennarz W., ed.), pp. 85-160. Plenum Press, New York (1980)). However, new studies by the present inventors established that the enzyme activity in fetal and cancer tissues is capable of transferring a GalNAc residue to a defined threonine residue on a polypeptide chain occuring in normal cells. This suggests that the specificity and avidity of this enzyme is onco-developmentally regulated.

The presence of multiple O-linked oligosaccharides at the N-terminal region of glycophorin has a role in formation of blood groups M and N epitope (Lisowska, E. and Wasniowaka, K. (1978) *Eur. J. Biochem.* 88, 247-252 (1978) and Sadler, J. E., et al. (1979) *J. Biol. Chem.* 254, 2112-2119). However, specificity of these blood groups resides in the difference of primary amino acid sequence (Lisowska, E. and Wasniowaka K. (1978) *Eur. J. Biochem.* 88, 247-252 and Sadler, J. E., et al. (1979) *J. Biol. Chem.* 254, 2112-2119 (1979)).

The FN isotypes which differ in polypeptide domain composition are believed to be the result of alternative splicing of the precursor mRNA from a single gene (Hynes, R. (1985) *Ann. Rev. Cell Biol.* 1, 67-90). Alternative splicing yielding three regions designated as IIICS extra domain I (ED-I), and extra domain II (ED-II), have been identified (Gutman, A. and Kornblihtt, A. R. (1987) *Proc. Natl. Acad. Sci. USA* 84, 7179-7182 and Zardi, L., et al. (1987) *EMBO J.* 6, 2337-2342). Variability in the IIICS region explains the difference between larger and smaller subunits of FNs. Although ED-I and ED-II are highly expressed in the majority of FNs from transformed or tumor-derived cells (Gutman, A. and Kornblihtt, A. R. (1987) *Proc. Natl. Acad. Sci. USA* 84, 7179-7182 and Zardi, L., et al. (1987) *EMBO J.* 6, 2337-2342), expression of ED regions in FNs is basically different from the onfFN epitope induced by glycosylation.

A single glycosylation at the threonine residue of the VTHPGY hexapeptide, which produces an oncofetal epitope, is catalyzed by onco-developmentally regulated α-N-acetylgalactosaminyltransferase. As a result of further research and investigations, the present inventors have isolated and characterized this new α-N-acetylgalactosaminyltransferase which represents an essential key to formulating a new class of oncofetal epitopes. A systematic study may reveal that oncodevelopmentally regulated α-N-acetylgalactosaminylation produces a number of oncofetal epitopes by O-linked glycoylation in glycoproteins other than FN. It is also possible that this aberrant O-glycosylation in oncofetal tissue results in enhanced synthesis of Tn and sialyl Tn epitopes, which constitute a class of tumor antigens (Hirohashi, E., et al. (1985) *Proc. Natl. Acad Sci. USA* 82, 7039-7043 and Kjeldsen, T., et al (1988) *Cancer Res.* 48, 2214-2220 ).

The present inventors have also developed a method of detecting tumor cells by assaying for the presence of this enzyme in cell homogenates.

As mentioned above, the onco-developmentally regulated α-N-acetylgalactosaminyltransferase of the present invention has the following characteristics:

(a) Activity in Various Cells and Tissues—present in human fetal lung fibroblasts, hepatoma tissues and placenta, but absent from normal adult liver, lung, kidney and spleen tissues;

(b) Substrate Specificity—acts on polypeptides comprising a sequence of val-thr-his-pro-gly-tyr by catalyzing α-N-acetylgalactosaminylation at the thr residue of the sequence;

(c) Requirements for Metal Ion—requires metal ion for activity in 25 mM tris buffer, pH 7.6;

(d) Optimal pH—optimal pH is about 7.6 assayed in hepatoma cell homogenate in tris buffer and at a pH of about 6 to about 7 assayed in hepatoma cell homogenate enzyme activity is higher in 2(N-morpholino)ethanesulfonic acid than in cacodylate buffer; and (e) Km—apparent Km for UDP-GalNAc is about 48 $\mu$M.

In order to determine the activity of the onco-developmentally regulated α-N-acetylgalactosaminyltransferase in various cells and tissues, the cells and/or tissues are homogenized and incubated with an appropriate substrate such as val-thr-his-pro-gly-tyr (VTY), thr-pro-phe-val-thr-his-pro-gly-tyr-asp-thr-gly-asn-gly-ile (TPI), thr-pro-phe-val-thr-his-pro-gly-tyr-asp-thr-gly-asn-gly-ile-gln-leu-pro-gly-thr-ser-gly-gln-gln-pro-ser-val-gly-gln-gln (TPQ) or norFN. Controls can be run with onfFN and no substrate. It is preferable to test each cell or tissue sample at multiple concentrations. Further, a preferred substrate is TPI.

The reaction mixture is preferably a Tris buffer solution consisting of Tris, magnesium ion and calcium ion and having a pH of about 7.6. The homogenate in the buffer solution is mixed with the synthetic peptide or other peptide, such as norFN or onfFN and labeled GalNAc along with an excess of unlabeled GalNAc is added. A preferred label for the GalNAc is UDP[$^3$H]-GalNAc.

The mixture is incubated for a suitable amount of time at a suitable temperature, for example for about 2 hours at about 37° C. and then centrifuged at about 10,000 rpm for 30 min in order to pellet the cellular debris. The reactive substrate is then separated from the supernatant by a suitable method, such as, for example, applying the supernatant to a sepharose 4B precolumn followed by a FDC-6 immunoaffinity column containing purified FDC-6 antibody as described, for example, in Matsuura, H., et al. (1988) *J. Biol. Chem.* 263, 3314-3322. The reactive substrate can also be removed from the supernatant by immunoprecipitation with a suitable antibody such as FDC-6 as described, for example, in Bigler, R. D., et al. (1988) *J. Immunol.* 141, 21. The column or immunoprecipitate is then washed with a suitable buffer and, if on a column, eluted, for example, with potassium thiocyanate, in the same buffer solution. The eluate or precipitate and washings are pooled and the aliquots counted.

The hybridoma cell line producing the antibody FDC-6 is publicly available from the American Type Culture Collection, Rockville, Md.

The peptides are synthesized by conventional methods using a peptide synthesizer (Mahoney, W. C. and Hermodson M. A. (1980) *J. Biol. Chem.* 255, 11999-11203).

Human onfFN can be prepared by affinity column chromatography with a gelatin-Sepharose column as described by Engvall, E. and Ruoslahti, E. ((1977) *Int. J. Cancer* 20, 1-5) from the culture medium of human hepatoma cell line HUH-7 (Matsuura, H., et al. (1988) *J.*

Biol. Chem. 263, 3314–3322). Human norFN can be prepared from outdated human plasma using a gelatin-Sepharose column.

A detailed protocol for determining enzyme activity in various cells and tissues is described below in Example 4.

The substrate specificity can be determined in a manner analogous to that described above for determining the activity in various cells and tissues. For this assay, it is preferred to use a hepatoma cell homogenate, such as a HUH-7 homogenate, as the source of the enzyme activity.

A detailed protocol for determining substrate specificity is set forth below in Example 1. From such experiments, it has been determined that the onco-developmentally regulated α-N-acetylgalactosaminyltransferase of the present invention acts on polypeptides comprising a sequence of val-thr-his-pro-gly-tyr by catalyzing α-N-acetylgalactosaminylation at the thr residue of the sequence.

The requirement for metal ion for activity in a particular buffer or with a particular substrate can also be determined by a method analogous to that described above for determining the activity of the enzyme in various cells and tissues. However, in these assays, the metal ion is varied.

In the present case, the requirement for metal ion for the onco-developmentally regulated α-N-acetylgalactosaminyltransferase was determined in 25 mM Tris buffer, pH 7.6, supplemented with 20 mM $MnCl_2$, 10 mM $MgCl_2$, 1 mM $CaCl_2$ and combinations of two of these or 1 mM EDTA. The results indicate that the enzyme has some requirement for metal ion and, in particular, enzyme activity detected with TPI peptide as acceptor was highest in the presence of $Mg^{2+}$ and $Ca^{2+}$. Further, divalent cation $Mn^{2+}$ can, under these conditions, substitute for $Mg^{2+}$. Enzyme activity is totally abolished in the presence of EDTA.

Determination of the metal ion requirements of the onco-developmentally regulated α-N-acetylgalactosaminyltransferase of the present invention is described in detail in Example 3.

The optimal pH for the onco-developmentally regulated α-N-acetylgalactosaminyltransferase of the present invention can be determined in a manner analogous to that described above for determining the activity in various cells and tissues, except that different buffer solutions are used. For this assay, it is preferred that the enzyme source be hepatoma cells, for example HUH-7. Determination of the effect of pH on the activity of the enzyme is described in detail in Example 2 and FIG. 1A.

The results indicated that the optimal pH of the onco-developmentally regulated α-N-acetylgalactosaminyltransferase of the present invention in hepatoma cell homogenate is about 7.6 in Tris buffer. Further, activities at a pH at about 6 to about 7 were higher in MES (2(n-morpholino)ethanesulfonic acid) than in cacodylete buffer.

The pH requirements are quite different from those reported previously for polypeptide α-N-acetylgalactosaminyltransferase of submaxillary glands ((McGuire, E. J. and Roseman, S. (1967) *J. Biol. Chem.* 242, 3745 Kobata, A. (1968) *Biochem. Biophys. Res. Commun.* 32, 272 (1968) and Hill, H. D., et al. (1977) *J. Biol. Chem.* 252, 3799–3804 (1977)) or plasma (Whithead, J. S., et al (1974) *J. Biol. Chem.* 249, 3442–3447 (1974)).

The apparent Km for UDP-GalNAc can be determined by generating a Hanes-Woolf plot of saturation data obtained by varying the UDP-GalNAc concentration at a constant cellular or tissue protein concentration and a constant substrate concentration. A preferred substrate for this assay is TPI.

Figure 1A:
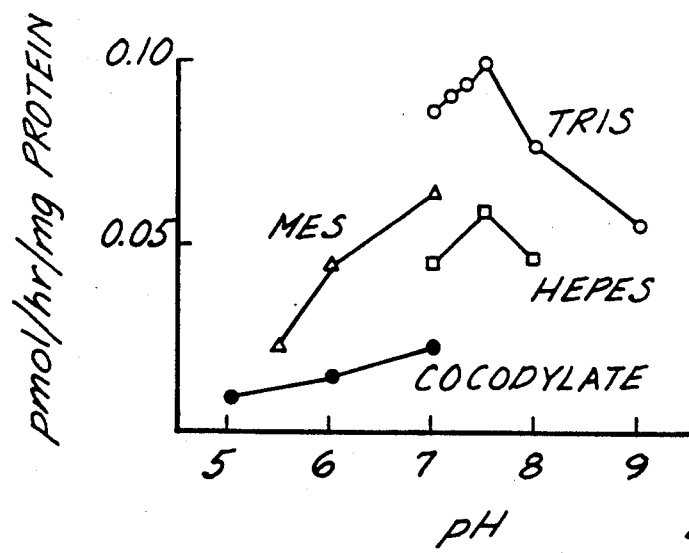
FIG. 1 shows the results of various experiments conducted to characterize onco-developmentally regulated α-N-acetylgalactosaminyltransferase.
Figure 1B:
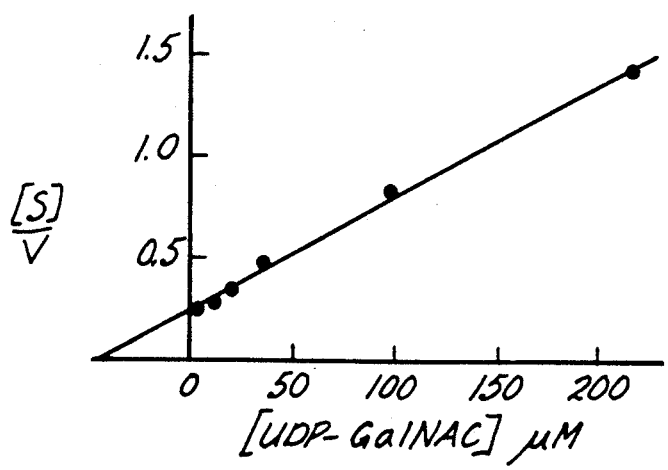

A Hanes-Woolf plot of saturation data for the onco-developmentally regulated α-N-acetylgalactosaminyltransferase of the present invention is shown in FIG. 1B and was generated as described in Example 2 below. From this Hanes-Woolf plot, it was determined that the apparent Km for UDP-GalNAc is about 48 μM.

Based on the above experiments, a reaction mixture for obtaining optimal enzyme activity was determined to contain 12.5 μmol Tris, pH 7.6, 200 nmol TPI 0.3 nmol UDP[$^3$H]-GalNAc, 25 nmol UDP-GalNAc, 5 μmol $MgCl_2$ and 0.5 μmol $CaCl_2$.

Under these conditions a linear increase of α-GalNAc transfer to the synthetic peptide TPI was observed for two hours followed by decreasing activity, which may have been due to degradation of the peptide. This experiment and the results thereof are described in Example 2 and shown in FIG. 1C respectively.

Additionally, the present inventors have found that the activity of the onco-developmentally regulated α-N-acetylgalactosaminyltransferase of the present invention is found only in the pellet of the particulate membrane fraction at a 100,000×g centrifugation for 1 hour. The particulate membrane fraction can be prepared according to the method of Holmes, E. H. et al. ((1985) *J. Biol. Chem.* 260, 7619–7627). Also, solubilization of the enzyme using a variety of detergents, including Triton X-100, Empigen BB, and CHAPSO (3-(3-cholamidopropyldimethylammonio)-1-(20-hydroxy-1-propanesulfonate), does not enhance enzyme activity and thus various tissue homogenates without detergent are suitably used to observe incorporation of GalNAc from UDP-GalNAc to synthetic polypeptides with a defined sequence.

Also provided by the present invention are two novel methods of isolating the onco-developmentally regulated α-N-acetylgalactosaminyltransferase.

Purification of the onco-developmentally regulated α-N-acetylgalactosaminyltransferase can be achieved by a variety of methods, including those previously used to purify glycosyltransferases. Shaper, N. L., et al. (1986) *Proc. Natl. Acad. Sci. USA* 83, 1573–1577, Narimatsu, H., et al. (1986) *Proc. Natl. Acad. Sci. USA*, 83, 4720–4724, and Humphreys-Beher, M. G., et al. (1986) *Proc. Natl. Acad. Sci. USA* 83, 8918–8922.

Further, onco-developmentally regulated α-N-acetylgalactosaminyltransferase can be isolated from a variety of oncofetal tissues. Preferred tissues include human hepatoma HUH-7 cells and human placenta.

Preferred purification methods include substrate immobilized affinity chromatography; for example, UDP-hexanolamine-Sepharose chromatography (Beyer, T. A., et al. (1981) *Advances in Enzymology* 52, 24–158), and val-thr-his-pro-gly-tyr-Sepharose 4B chromatography or tyr-pro-phe-val-thr-his-pro-gly-tyr-asp-thr-gly-asn-gly-ile-Sepharose 4B chromatography. The latter being made by first synthesizing the peptide in a peptide synthesizer or purchasing it from custom peptide synthesis sources (for example, Cambridge Research Biochemicals, Inc., 10 East Merrick Road, Valley Stream, N.Y.) and thereafter coupling the peptide to a cyanogen bromide-activated Sepharose 4B.

More specifically, one new method for isolating the onco-developmentally regulated α-N-acetylgalactosaminyltransferase consists of contacting oncofetal tissue with an immobilized polypeptide substrate comprising a sequence of val-thi-his-pro-gly-tyr, thereby forming an affinity complex, washing the complex, and eluting the α-N-acetylgalactosaminyltransferase therefrom.

An alternative method consists of first labeling the peptide substrate with a detectable marker and reacting the peptide substrate with a bifunctional photoreactive cross-linking agent. The peptide substrate, so modified, is then contacted with oncofetal tissue homogenate and the mixture is thereafter exposed to ultraviolet radiation sufficient to cross-link the labeled peptide to the onco-developmentally regulated α-N-acetylgalactosaminyltransferase. The radiolabeled enzyme is thereafter purified by conventional procedures, including reverse phase HPLC with an acetonitrile gradient in aqueous trifluoroacetic acid.

For both isolation methods suitable polypeptide substrates include: val-thr-his-pro-gly-tyr (VTY), thr-pro-phe-val-thr-his-pro-gly-tyr-asp-thr-gly-asn-gly-ile (TPI), thr-pro-phe-val-thr-his-pro-gly-tyr-asp-thr-gly-asn-gly-ile-gln-leu-pro-gly-thr-ser-gly-gln-gln-pro-ser-val-gly-gln-gln (TPQ), and normal fibronectin (norFN). TPI is preferred.

The present invention also provides a method of detecting tumor cells by assaying for activity of the onco-developmentally regulated α-N-acetylgalactosaminyltransferase of the present invention. The method of detecting tumor cells is conducted by incubating a tissue homogenate suspected of having tumor cells with labeled α-N-acetylgalactosamine (α-GalNAc) and a polypeptide substrate comprising a sequence of val-thr-his-pro-gly-tyr under conditions sufficient to catalyze α-N-acetylgalactosaminylation of the thr-residue to thereby form a labeled polypeptide substrate wherein the thr residue of the above-mentioned sequence is glycosylated. The presence of labeled polypeptide substrate is then determined as a measure of oncogenesis.

Suitable polypeptide substrates are the same as those described above for the methods of isolating the enzyme and the substrate TPI is preferred.

Preferred conditions for incubating the homogenate are those described above for optimal enzyme activity which were determined from the various experiments conducted in order to characterize the enzyme.

In an especially preferred embodiment, the method of detecting tumor cells employs the monoclonal antibody FDC-6 for determining the presence of the labeled polypeptide substrate.

This method is conducted by incubating a cell or tissue homogenate with a medium containing a suitable substrate as described above, radiolabeled UDP-GalNAc, and calcium and magnesium salts. A preferred labeled UDP-GalNAc is UDP[$^3$H]GalNAc. After incubating this mixture under conditions suitable for transforming the peptide substrate to the corresponding radiolabeled glycosylated reaction product, the mixture is then centrifuged and the supernatant is contacted with immobilized monoclonal antibody FDC-6 specific for that reaction product. The bound radiolabeled glycosylated peptide substrate is then washed, eluted, and the radiolabel measured in the eluate. The amount of radiolabel in the eluate is correlated with the level of onco-developmentally regulated α-N-acetylgalactosaminyltransferase activity in the tissue homogenate which positively indicates the presence of tumor cells in the biopsied tissue or plasma sample.

In another aspect, the invention provides a diagnostic test kit for detecting tumor cells in a sample suspected of containing tumor cells. The kit comprises as separate components labeled α-N-acetylgalactosamine and a polypeptide substrate comprising a sequence of val-thr-his-pro-gly-tyr. The kit may also contain an antibody, free or immobilized, specific to val-thr(α-GalNAc)-his-pro-gly-tyr.

A preferred labeled α-N-acetylgalactosamine is UDP[$^3$H]-GalNAc. Suitable polypeptide substrates include those described above for the methods of purifying the onco-developmentally regulated α-N-acetylgalactosaminyltransferase of the present invention and a preferred substrate is TPI.

When the above-mentioned substrates are used, a preferred antibody is the monoclonal antibody FDC-6.

The diagnostic kit may also contain other reagents necessary to optimally activate oncofetal-developmentally regulated α-N-acetylgalactosaminyltransferase.

EXAMPLES

The present invention will now be described by reference to specific examples, which are not meant to be limiting.

Unless otherwise indicated, all percents, ratios, etc. are by volume.

EXAMPLE 1

Determination of Oncofetal Developmentally Regulated α-N-Acetylgalactosaminyltransferase Activity toward Different Substrates $8 \times 10^7$ hepatoma cells (HUH-7) cultured in serum-free medium (Dulbecco-Modified Eagles Medium) were homogenized in a Potter-Elvehjem homogenizer with 200 μl of distilled water. 300 μl of tris buffer solution, consisting of 25 mM tris, 10 mM MgCl$_2$ and 1 mM CaCl$_2$, pH 7.6, was added. 500 μl of cell homogenate in the buffer solution was mixed with 200 nmol of synthetic peptide shown in the Table below, norFN, or onfFN. 0.3 nmol UDP[$^3$H]-GalNAc (specific activity 8.7 Ci/mmol, New England Nuclear Research Product) and 25 nmol UDP-GalNAc were added and incubated for 2 hrs at 37° C. The incubation mixture was centrifuged at 10,000 rpm for 30 min. Supernatant was applied onto a 0.5 ml Sepharose 4B precolumn, followed by a 0.5 ml FDC-6 immunoaffinity column containing 10 mg of purified FDC-6 antibody/ml as described by Matsuura, H. et al. ((1988) *J. Biol. Chem.* 263, 3314–3322). Immunoprecipitation using 200 μl of FDC-6 binding Sepharose 4B was also performed as described by Bigler R. D. et al ((1988) *J. Immunol.* 144 21). Supernatants were incubated for 1 hr at 20° C. The column or immunoprecipitate was washed with 1M NaCl in 50 mM Tris buffer, pH 7.4, and eluted with 2.5M potassium thiocyanate in the same buffer solution. The eluate and washings were pooled and aliquots were counted. The same incubation mixture without addition of synthetic peptides or FN was used as a control.

Peptides were synthesized using a peptide synthesizer (Applied Biosystems 430A). The symmetric anhydrides of t-butoxycarbonyl-protected amino acids were used for dicyclohexylcarbodiimide-mediated coupling to the peptide chain. Phenylacetamidomethyl resin was used as a solid support. Peptides were cleaved from the support by treatment with anhydrous hydrogen fluoride for 1 hr at 0° C. in the presence of 10% (v/v) anisole and 1% (v/v) dimethyl sulfide. After extraction with 50%

(v/v) acetic acid, the peptides were chromatographed on Bio-Gel P4 using 1M acetic acid as eluant. Fractions containing peptides were lyophilized and further purified to homogeneity by reverse-phase HPLC, using a Synchropak RP-P C18 column (Syn Chrom. Linden, Ind.) as previously described (Mahoney, W. C. and Hermodson, M. A. (1980) *J. Biol. Chem.* 255 11199-11203).

Human onfFN was prepared by affinity column chromatography with a gelatin-Sepharose column as described by Engvall, E. and Ruoslahti, E. ((1977) *Int. J. Cancer* 20, 1-5) from the culture medium of human hepatoma cell line HUH-7 (Matsuura H., et al. (1988) *J. Biol. Chem.* 263, 3314-3322). Human norFN was prepared from outdated human plasma using a gelatin-Sepharose column.

The results are shown in the Table below. The one-letter codes used to denote amino acids are: D, Asp; F, Phe; G, Gly; H, His; I. Ile; L, Leu; N, Asn; P, Pro; Q, Gln; S, Ser; T, Thr; V, Va; Y, Tyr.

TABLE

Specific Activity to various acceptors of α-N-acetylgalactosaminyltransferase in crude homogenates of human hepatoma cells (HUH-7)

| Code | Acceptor | Activity (pmol/hr/mg protein) |
| --- | --- | --- |
| VTY | VTHPGY | 0.03 |
| TPI | TPFVTHPGYDTGNGI | 0.11 |
| TPQ | TPFVTHPGYDTGNGI-QLPGTSGQQPSVGQQ | 0.06 |
| norFN | normal fibronectin | 0.04 |
| orfFN | oncofetal fibronectin | <0.001 |
| control | — | <0.001 |

The results in the Table establish that the synthetic peptides VTY, TPI and TPQ as well as norFN are all suitable substrates for detecting the presence of α-N-acetylgalactosaminyltransferase in crude homogenates of human tumor cells.

EXAMPLE 2

Characterization of Onco-developmentally Regulated α-N-Acetylgalactosaminyltransferase a. Effect of pH The effect of pH on α-N-acetylgalactosaminyltransferase was examined with different buffer solutions.

Hepatoma cells (HUH-7) were homogenized as described in Example 1 and incubated with synthetic peptide TPI as described in Example 1, except that the following different buffer solutions were used: 25 mM MES (2(N-morpholino)ethanesulfonic acid, Sigma Chemical Co.), pH range 5.4 to 7.0; 25 mM cacodylate, pH range 5 to 7; 25 mM HEPES (N-2-hydroxyethylpiperazine-N'-2-ethanesulfonic acid, Sigma), pH range 7 to 8; or Tris, pH range 7-9, all in the presence of 10 mM $MgCl_2$ and 1 mM $CaCl_2$. After incubating for 2 hrs at 37° C. the incubation mixtures were centrifuged as described in Example 1 and the supernatants applied onto a Sepharose 4B precolumn, followed by an FDC-6 immunoaffinity column also as described in Example 1. The pH of the incubation mixtures was adjusted to 7.4 before application to the FDC-6 immunity affinity column. After incubating for 1 hour at 20° C. the immunoaffinity column was washed and eluted as described in Example 1 and the eluate counted.

The results are shown in FIG. 1A.

FIG. 1A shows that the optimal pH of the onco-developmentally regulated α-N-acetylgalactosaminyltransferase present in hepatoma cell homogenate was about 7.6 in Tris buffer and that the activity of onco-developmentally regulated α-N-acetylgalactosaminyltransferase at a pH of about 6 to about 7 was higher in MES buffer than in cacodylate buffer.

b. Effect of UDP-GalNAc concentration

A Hanes-Woolf plot of saturation data was obtained by varying UDP-GalNAc concentration from 0.6 μM to 200 μM. The reaction as conducted as described in Example 1 in the presence of 100 mg protein of hepatoma cell homogenate and 200 nmol TPI. The specific activity of the UDP[$^3$H]-GalNAc used was $4 \times 10^6$ cpm/nmol. The reacted samples were also treated as described in Example 1.

The results are shown in FIG. 1B.

From the data in FIG. 1B the apparent Km for UDP-GalNAc is calculated as about 48 μM.

c. Variation of Incubation Time

In order to determine the kinetics of α-GalNAc transfer to synthetic peptide, a reaction mixture containing 12.5 μmol Tris, pH 7.6, 200 nmol TPI, 0.3 nmol UDP[$^3$H]-GalNAc, 25 nmol UDP-GalNAc, 5 μmol $MgCl_2$, 0.5 μmol $CaCl_2$ and homogenized hepatoma cells (HUH-7) was incubated for 10 min. to 24 hours at 37°. A parallel control was run without TPI. At the end of the incubation periods, the samples were treated as described in Example 1.

Figure 1C:
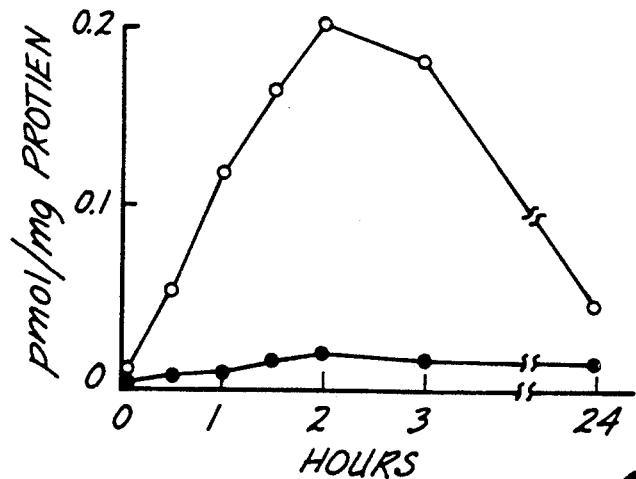

The results are shown in FIG. 1C, wherein the open circles represent the reaction conducted with TPI and the closed circles represent the control.

From the results shown in FIG. 1C it is seen that α-GalNAc transfer to synthetic peptide is linear for up to about 2 hours at which time the activity begins to decrease. The decrease could have been due to degradation of the peptide TPI.

EXAMPLE 3

Determination of Metal Ion Requirements of Onco-developmentally Regulated α-N-acetylgalactosaminyltransferase Hepatoma cell (HUH-7) homogenates and the synthetic and natural peptides set forth in the Table in Example 1 were prepared as in Example 1 and incubated as described in Example 1 using 25 mM Tris buffer, pH 7.6; supplemented with 20 mM $MnCl_2$, 10 mM $MgCl_2$, 1 mM $CaCl_2$ and combinations of two of these or 1 mM EDTA.

As can be seen from the Table in Example 1, in the presence of $Mg^{2+}$ and $Ca^{2+}$, enzyme activity is highest with TPI as substrate. Further the divalent cation $Mn^{2+}$ could be substituted for $Mg^{2+}$. Enzyme activity was totally abolished in the presence of EDTA.

Thus the enzyme has a requirement for metal ions for activity in 25 mM tris buffer, pH 7.6.

EXAMPLE 4

Onco-Developmentally Regulated α-N-acetylgalactosaminyltransferase

Activity in Various Cells and Tissues

In order to demonstrate that the oncodevelopmentally regulated α-N-acetylgalactosaminyltransferase of the present invention is indeed specific to fetal cells and tumor cells and not found in cells from normal tissue, multiple concentrations of protein from various tissues and cells were incubated with TPI under the same conditions as described in Example 1 and the presence or absence of onco-developmentally regulated acetylgalactosaminyltransferase was determined, also as described in Example 1. Specifically, homogenized human placenta tissue, hepatoma tissue, normal adult liver, lung, spleen and kidney tissue, HUH-7 cells and human fetal lung fibroblast cells (WI-38) were used as the enzyme source.

The results are shown in FIG. 2.

The data in FIG. 2 indicate enzyme activity in human placenta and hepatoma tissue but not in normal liver, lung, spleen and kidney tissues. HUH-7 and WI-38 cells also showed enzyme activity.

EXAMPLE 5

Purification of the Onco-developmentally Regulated α-N-acetylgalactosaminyltransferase from Human Hepatoma HUH-7 Cells and Human Placenta a. Affinity chromatoqraphy Human hepatoma HUH-7 cells or human placenta are utilized as an enzyme source due to their high α-N-acetylgalactosaminyltransferase activity. Placenta is used after extensive washing with phosphate buffered saline. Hepatoma cells are cultured in serum-free medium (Dulbecco-Modified Eagles Medium). Hepatoma cells or placenta tissue are homogenized in two volumes of 50 mM Tris, pH 7.6, by a Potter-Elvehjem homogenizer and centrifuged at 27,000×g to separate soluble proteins from the membrane fraction. The membrane bound α-N-acetylgalactosaminyltransferase is solubilized by homogenization twice in the presence of the above buffer containing 0.2% Triton X-100 and centriguted for 1 hour at 100,000×g. The combined solubilized enzyme fractions are then subjected to a variety of chromatographic steps to yield the homogeneous enzyme. These steps include affinity chromatography on UDP-hexanolamine-Sepharose. The solubilized enzyme is applied to the above column equilibrated with the homogenization buffer and washed with 10 bed volumes of fresh buffer, thereafter the enzyme is eluted with a linear NaCl gradient to a final concentration of 1M. Fractions containing activity are pooled and either concentrated by ultrafiltration and desalted by chromatography on Sephadex G-25 or diluted with 50 mM Tris, 10 mM MgCl$_2$, 1 mM CaCl$_2$, pH 7.6, and reapplied to another UDP-hexanolamineSepharose column, washed, and the enzyme is specifically eluted with buffer containing 5 mM UDP.

Additional affinity chromatography utilizes synthetic peptides comprising the sequence val-thr-his-pro-gly-tyr coupled to cyanogen bromide-activated Sepharose 4B. Enzyme fractions after purification on UDP-hexanolamine-Sepharose are first passed over Sephadex G-25 to remove salt or UDP and applied to the peptide affinity column in 50 mM Tris, 10 mM MgCl$_2$, 1 mM CaCl$_2$, pH 7.6. The column is washed extensively and the enzyme eluted by a linear NaCl gradient. Fractions containing activity are then pooled and desalted. Further purification, if necessary, can be achieved using FPLC (fast protein liquid chromatography) (Markey, F. (1948) *FEBS Lett.* 167, 155–159) with a gel filtration column in order to obtain the homogeneous enzyme. Steps in the purification procedure are monitored by measurement of the enzyme's specific activity and purity by SDS-polyacrylamide gel electrophoresis (Laemmli, U. K. (1970) *Nature* 277, 680–685).

b. Photoreactive cross-linking

The photoreactive cross-linking agents, N-hydroxysuccinimidyl-4-azidobenzoate (HSAB) (Ji. I., and Ji T. H. (1980) *Proc. Natl. Acad. Sci. USA* 77, 7167–7170) or sulfosuccinimidyl 2-(p-azidosalicylamido)-1,3′-dithiopropionate (SASD) (Shanahan, M. F., et al. (1985) *J. Biol. Chem.* 260, 10897–10900) are useful for tightly binding the enzyme with the synthetic peptide substrates comprising the sequence val-thr-his-pro-gly-tyr. Iodination of synthetic peptides is conducted using Iodobead (Markwell, M. A. K. (1982) *Anal. Biochem.* 125, 427–432) or the Bolton-Hunter Reagent (Bolton, A. E. and Hunter, W. M. (1973) *Biochem. J.* 133, 529–539). Reductive alkylation can be performed using $^{14}$C-formaldehyde (Rice, R. H. and Means, G. E. (1971) *J. Biol. Chem.* 246, 831–832) as an alternative labeling method. HSAB is added to radiolabeled synthetic peptide solution and incubated (Ji. I. and Ji. T. H. (1980) *Proc. Natl. Acad. Sci. USA* 77, 7167–7170). HSAB linking of the radiolabeled synthetic peptide is conducted by incubating the HSAB linked hexapeptide with cell homogenate and exposure to UV irradiation. Alternatively, the iodinatable photoreactive cross-linking agent, SASD, is used. $^{125}$I-SASD is prepared with iodobead, and 10 μl Na$^{125}$I (Amersham) essentially as previously reported methods (Shanahan, M. F., et al., *J. Biol. Chem.* 260, 10897–10900 (1985)). $^{125}$I-SASD linking synthetic peptide is prepared by incubating the synthetic peptide with $^{125}$I-SASD. This reaction mixture is then passed through a P-2 column (Bio-Rad). The void volume peak, consisting of $^{125}$I-SASD-peptide is then pooled.

SDS-polyacrylamide gel electrophoresis and immunoblotting (Towbin, H., et al. (1979) *Proc. Natl. Acad. Sci. USA* 76, 4350–4354) is then performed and analyzed of the cross-linked enzyme. The cross-linked enzyme is purified using reverse-phase HPLC with an acetonitrile gradient in aqueous trifluoroacetic acid (Mahoney, W. C. and Hermodson, M. A., *J. Biol. Chem.* 255, 11199–11203 (1980)).

EXAMPLE 6

Assay of the Purified α-N-acetylgalactosaminyltransferase

The following conditions are used for assay during purification of the enzyme. The reaction mixture contains 100 μl of 50 mM Tris, 10 mM MgCl$_2$, 1 mM CaCl$_2$, pH 7.6, 100 μg synthetic peptide 0.35 nmol UDP$^3$H-)GalNAc, and 15–150 μg protein in a total volume of 200 μ. The reaction mixture is incubated for 2 hours at 37° C. and centrifuged at 10,000 rpm for 30 min. Supernatant is incubated with 50 μl of FDC-6-Sepharose, for 30 min. at 20° C. washed with centrifugation. Radioactivity bound to FDC-6-Sepharose is counted in a liquid scintillation counter. The reaction mixture without synthetic peptide is also counted as a control. One unit of activity is defined as transfer of one picomol of GalNAc per hour under the conditions of the assay.

While the invention has been described in detail and with reference to specific embodiments thereof, it will be apparent to one skilled in the art that various changes and modifications can be made therein without departing from the spirit and scope thereof.

What is claimed is;

1. An onco-developmentally regulated α-N-acetylgalactosaminyltransferase isolated as a component of a particulate membrane fraction separated from cell and tissue homogenates and having the following characteristics:
   (a) is present in human fetal lung fibroblasts, hepatoma tissues and placenta, but absent from normal adult liver, lung, kidney, and spleen tissues;
   (b) acts on polypeptides comprising a sequence val-thr-his-pro-gly-tyr by catalyzing a transfer of a N-acetylgalactosaminyl residue from UDP-GalNAc donor to the thr residue acceptor of the sequence;
   (c) requires metal ion for activity in 25 mM Tris buffer, pH 7.6;
   (d) optimal pH is about 7.6 assayed in hepatoma cell homogenate in Tris buffer, and at a pH of about 6 to about 7 assayed in hepatoma cell homogenate in Tris buffer, and at a pH of about 6 to about 7 assayed in hepatoma cell homogenate enzyme activity is higher in 2(N-morpholino)ethanesulfonic acid than in cacodylate buffer;
   (e) apparent Km for UDP-GalNAc in the transfer is about 48 μM; and
   (f) enzyme activity not enhanced by Triton X-100.

* * * * *

UNITED STATES PATENT AND TRADEMARK OFFICE
CERTIFICATE OF CORRECTION

PATENT NO. : 5,177,015  Page 1 of 2
DATED : January 5, 1993
INVENTOR(S) : H. Matsuura et al It is certified that error appears in the above-indentified patent and that said Letters Patent is hereby corrected as shown below:

ON THE TITLE PAGE:

| | | |
|---|---|---|
| [56] "Publn." | 1st Publ. | "*Gropu*" should read --*Group*-- |
| [56] "Publn." | 3rd Publ. | "Ishihashi et al." should read --Ishibashi et al.-- |
| [56] "Publn." | 3rd Publ. | "Biophsy." should read --Biophys.-- |
| 1 | 3 | Please add --This invention was made with government support under grants CA42505 and CA23907 from the National Institutes of Health. The government has certain rights in the invention.-- |
| [57] "Abstr." | 5 & 6 | "characeris-tics" should read --characteristics-- |

UNITED STATES PATENT AND TRADEMARK OFFICE
CERTIFICATE OF CORRECTION

PATENT NO. : 5,177,015
DATED : January 5, 1993
INVENTOR(S) : H. Matsuura et al.

It is certified that error appears in the above-identified patent and that said Letters Patent is hereby corrected as shown below:

| | | |
|---|---|---|
| [57] "Abstr." | 20&21 | "2(N-morpholino)ethanelsulfonic" should read --2(N-morpholino)ethanesulfonic-- |
| [57] "Abstr." | 27 | "tumnor" should read --tumor-- |
| 1 | 16 | "antigens." should read --antigens,-- |
| 14 | 52&53 | "UDP$^3$H-)GalNAc," should read --UDP($^3$H)GalNAc,-- |

Signed and Sealed this

Eleventh Day of January, 1994

Attest:

BRUCE LEHMAN

*Attesting Officer*   *Commissioner of Patents and Trademarks*